United States Patent
Poncelet et al.

(10) Patent No.: US 6,440,308 B1
(45) Date of Patent: *Aug. 27, 2002

(54) METHOD FOR TREATING A PHOTOGRAPHIC PROCESSING BATH

(75) Inventors: Olivier C. Poncelet, Chalon sur Saone; Danielle M. Wettling, Chatenoy le Royal, both of (FR)

(73) Assignee: Eastman Kodak Company, Rochester, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 09/255,924

(22) Filed: Feb. 23, 1999

(30) Foreign Application Priority Data

Feb. 23, 1998 (FR) .............................................. 98 02363

(51) Int. Cl.$^7$ .............................................. B01D 15/00
(52) U.S. Cl. ...................... 210/638; 210/663; 210/688; 210/912
(58) Field of Search .............................. 210/638, 651, 210/663, 679, 688, 912; 430/398

(56) References Cited

U.S. PATENT DOCUMENTS

| 5,575,915 A | * 11/1996 | Nakamura et al. .......... 210/688 |
| 5,683,826 A | * 11/1997 | Poncelet et al. ............ 428/702 |
| 5,814,226 A | * 9/1998 | Tablarides et al. .......... 210/679 |
| 5,958,245 A | * 9/1999 | Martin et al. ................ 430/398 |
| 6,179,898 B1 | * 1/2001 | Poncelet et al. .............. 75/713 |

FOREIGN PATENT DOCUMENTS

| EP | 0 736 249 A1 | 10/1996 |
| WO | 96/09985 | 9/1995 |

* cited by examiner

Primary Examiner—Ivars Cintins
(74) Attorney, Agent, or Firm—Chris P. Konkol

(57) ABSTRACT

The present invention relates to a composite material in which an active organic compound is dispersed, as well as to an effluent treatment process, especially a photographic effluent treatment process. The composite material comprises an aluminosilicate organic-inorganic polymer matrix in fiber form comprising at least on the surface an organic radical having a —SH or —S(—CH$_2$)$_n$—S— function with n between 0 and 4 and in which an active organic compound is dispersed.

5 Claims, 1 Drawing Sheet

METHOD FOR TREATING A PHOTOGRAPHIC PROCESSING BATH

Figure 1:
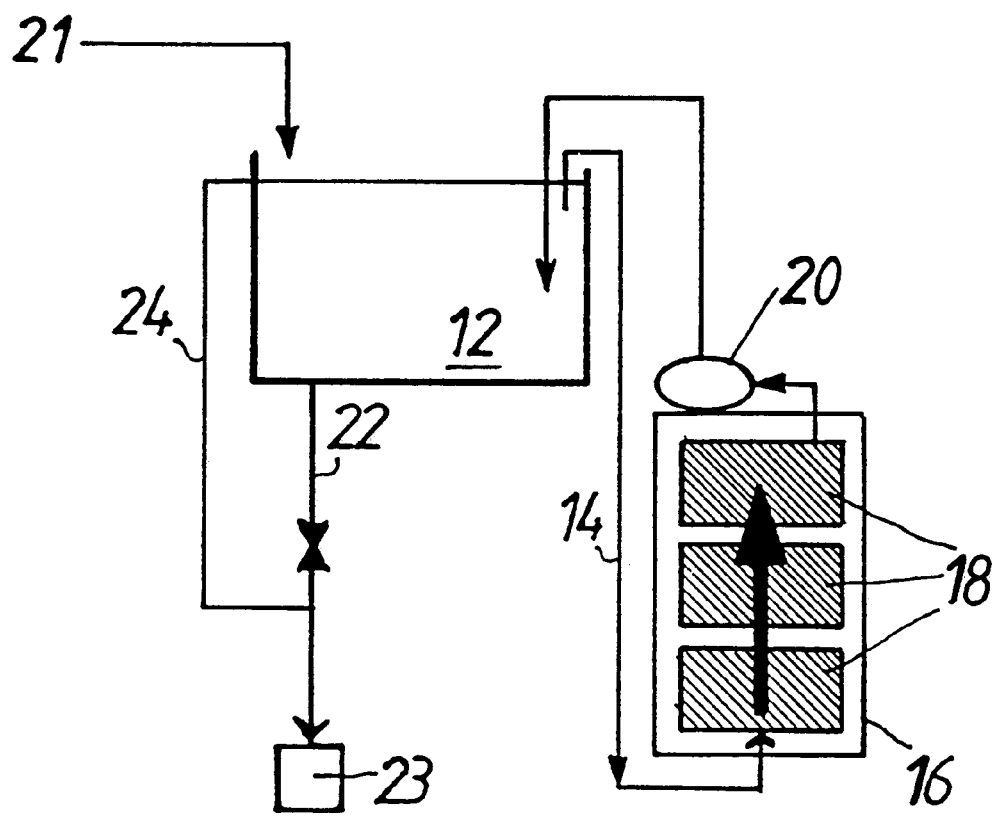

The present invention relates to a composite material having dispersed therein an active organic compound, as well as to an effluent treatment process, especially a photographic effluent treatment process.

Many manufacturing and processing methods generate effluents which, on the one hand, cannot be directly disposed of via the sewers because of their composition and, on the other hand, contain substances the recovery and re-use of which would be economically gainful. One example is the photographic processing industry, in which exposed silver halide photographic films and papers are treated in successive processing baths that are rich in chemicals. Such photographic film processing methods are well known (see for example, Chimie et Physique Photographiques; Pierre Glafkides, Vol. 2, Chap XL, pages 947–967).

In general, photographic processing comprises several processing baths and one or more wash and/or stabilization baths. The build-up in the wash and/or stabilization baths of substances carried over from the preceding processing steps is especially detrimental not only to the stability of developed photographic images and to the good keeping of sensitometric characteristics, but also to the possibility of recycling these wash and stabilization baths, or discharging them to the sewers. After processing, the wash and stabilization baths are found to contain inorganic compounds, such as iron, silver, thiosulfate, and sulfate ions, or organic compounds which are, either substances used for development, or products coming from the reaction of these substances during development, or from the step of fixing or bleach-fixing.

The problem of discharging silver to the sewers is especially important because of new standards that apply to photographic processing methods. There are notably standards that set the maximum volume of water that should be used for washing 1 $m^2$ of photographic material. In particular, for processing radiographs, the current French standard permits the use of 15 liters of water per $m^2$ of single-coated radiographic product to be processed and 30 liters of water per $m^2$ of double-coated radiographic product, with discharge to the sewers of water containing a maximum of 1 ppm of silver. Reducing the permissible volume of water produces wash baths that are more concentrated in silver and thus more difficult to decontaminate.

In addition, during the use of the baths, there is a biological growth, especially in the prebaths, the stabilization baths and the wash baths. If it is not controlled the growth of microorganisms causes the formation of sludge that can clog up the installation, deteriorate the process bath, and thus lead to a defective quality of the photographic image. Problems related to the growth of microorganisms are increasingly critical as the quantities of water permitted for processing photographic materials are increasingly restricted.

The use of biocides to prevent or limit biological growth in processing solutions is a current practice. For greater safety, quantities are used in excess of the strictly necessary amount. In this case, the water discharged into the environment contains large amounts of biocides, which create problems for treatment plants that use microorganism activity for treating effluents.

Therefore it would be desirable to provide a new process which can reduce the quantity of silver in ionic form contained in the photographic effluent and which can deliver a controlled amount of active organic compound, such as a biocide, in the effluent. It is also useful to have a process that is easy to apply and economic.

This objective is achieved with a composite material which comprises an aluminosilicate organic-inorganic polymer matrix in fiber form comprising at least on the surface an organic radical having a —SH or —S(—$CH_2$)$_n$—S— function with n between 0 and 4 and in which an active organic compound is dispersed.

The present invention further relates to a process for obtaining such a composite material. This process comprises the hydrolysis in a basic medium of an alkylalkoxysilane of the formula $RSiR^1_x(OR^2)_{3-x}$ in which R is an alkyl group having a —SH or —S(—$CH_2$)$_n$—S— function with n between 0 and 4, $R^1$ and $R^2$ are independently a methyl or ethyl group, x is 0 or 1, in the presence of an active organic compound and an aqueous solution of an aluminosilicate inorganic polymer in fiber form comprising active hydroxyl groups on the surface. "Active hydroxyl groups" are groups capable of reacting with alkylalkoxysilane in an aqueous medium.

Finally the present invention relates to a treatment process for photographic effluents containing silver in ionic form, as well as a device for carrying out this process. The treatment process of the invention comprises contacting the composite material with the effluent.

The process of the present invention is especially efficient for treating photographic baths used for processing silver halide photographic materials. For photographic baths, the silver is in the form of an ionic complex.

The treatment process of the invention does not modify the properties of the effluent treated. In particular, the pH of the effluent before and after the invention treatment as well as the salt content of the effluent stay unchanged. In addition, the nature of the water making up the effluent to be treated does not modify the efficiency of the treatment.

In the scope of the invention, it is not worthwhile previously diluting the treated effluent.

The composite material according to the invention has the advantage of being photographically inert, so that there is no detrimental effect on the sensitometric characteristics of the final images.

In the description below, reference will be made to the drawing in which:

FIG. 1 is a diagram showing one embodiment of the treatment process of the present invention applied to the treatment of a photographic bath.

The composite material of the invention can be obtained from any aqueous solution of aluminosilicate polymer in fiber form having active hydroxyl groups on the surface of theses fibers. For example phyllosilicates such as imogolite can be used as aluminosilicate.

When an alkylalkoxysilane, as defined above, is hydrolyzed in a basic medium in the presence of an active organic compound and an aqueous solution of an aluminosilicate inorganic polymer in fiber form having surface hydroxyl groups that are active in aqueous solution, the alkoxy groups of the alkylalkoxysilane react with the aluminosilicate hydroxyl groups to form a stable covalent bond thus forming an organic-inorganic matrix. This reaction goes along with the gelling of the aluminosilicate during which the active organic compound is trapped in the organic-inorganic polymer matrix. The composite material of the present invention is thus obtained. When the composite material of the invention is put into contact with an aqueous effluent, the trapped active organic compound will be released slowly into this effluent.

In a preferred embodiment, the composite material of the invention is obtained from imogolite type aluminosilicate.

Imogolite is an aluminosilicate polymer that is in the form of fibers whose external surface comprises active hydroxyl groups. Imogolite exists in the natural state; it was first described by Wada in J. Soil Sci. 1979, 30(2), 347–355. Imogolite can be synthesized by different methods. Examples of synthesis are described in Farmer U.S. Pat. Nos. 4,252,779, 4,241,035 and 4,152,404. A synthetic imogolite was also described in Patent Application WO 96/13459.

The alkylalkoxysilanes that are useful for the invention can be mercaptoalkylalkoxysilanes of the formula HS—$(CH_2)_m$—$SiR^1_x(OR^2)_{3-x}$ wherein m is at least 1, $R^1$, $R^2$ and x being as defined above. Preferably m is from 1 to 4. The mercaptoalkylalkoxysilanes that are useful for the invention are for example 3-mercaptopropyltrimethoxysilane,
3-mercaptopropyltriethoxysilane,
3-mercaptopropylmethyldimethoxysilane,
(mercaptomethyl)methyldiethoxysilane,
(mercaptomethyl)dimethylethoxysilane.

For the invention, alkylalkoxysilanes comprising an organic radical having a —S—S— function, such as for example Bis[3(triethoxysilyl)propyl]tetrasulfite, can also be used. Alkylalkoxysilanes having a crown ether organic radical containing the —S—S— or —S$(CH_2)_n$—S— function, n being from 1 to 4 can also be used.

The hydrolysis of the alkylalkoxysilane is carried out at a pH of more than 7. This pH is achieved by adding a base to the reaction medium, for example $NH_4OH$, NaOH, KOH. The addition of the base to the reaction medium allows the phyllosilicate to gel.

In addition to the alkylalkoxysilane described above, an alkylalkoxysilane modified by another non-hydrolyzable organic radical can be added to the aluminosilicate. With a suitable choice of organic radical, the properties of the organic-inorganic polymers of the invention can be modified in order to increase their efficiency. For example, an alkylalkoxysilane whose alkyl group is an haloalkyl can be added.

In this case, the organic-inorganic matrix of the composite material of the invention contains a bromoalkyl or chloroalkyl organic radical on the surface of the fibers. As an example, the use of bromopropyltrimethoxysilane allows the efficiency of the composite material of the invention to be increased.

The active organic compound used in the present invention is an organic compound that is soluble in the effluent to be treated and that does not form covalent bonds with the organic-inorganic matrix, otherwise it would stay trapped in the material.

According to the one embodiment, the active organic compound is a biocide. In this case, the composite material of the present invention allows the growth of microorganisms in the effluent to be reduced or stopped, while preventing the discharge into the environment of large amounts of biocide.

This biocide can be a pesticide, an algicide, a fungicide or a bactericide.

Biocides useful in photographic baths are for example selected from among the following bactericides and fungicides:

1) derivatives of thiazole, such as the isothiazolinones, for example 1,2-benzisothiazolin-3-one,
2-methyl-4-isothiazolin-3-one, 2-octyl-4-isothiazolin-3-one and 5-chloro-2-methyl-4-isothiazolin-3-one,
2) derivatives of azoles, such as benzotriazoles, benzimidazoles,
3) sulfamide type agents, such as sulfanilamide,
4) organoarsenides such as 10–10'-oxybis-phenoxyarsine,
5) benzoic acid, sorbic acid,
6) quartenary salts of benzalkonium,
7) nitro alcohols.

The preferred compounds are benzisothiazolinones, for example 1,2-benzisothiazolin-3-one marketed under the tradename Proxel® by Zeneca, and isothiazolinones, for example the mixture of 5-chloro-2-methyl-4-isothiazolin-3-one and 2-methyl-4-isothiazolin-3-one marketed under the tradename Kathon® by Rohm and Haas.

The quantity of biocide required will depend on the composition and volume of photographic effluent to be treated (in the order of 5 to 20 $m^3$ per week for photographic processing laboratories), on the nature of the biocide, on the conditions of use of this effluent, on the possible extent of microorganism contamination, and on the time during which the growth of microorganisms is required to be limited. The process according to the invention allows the just necessary amount of biocide to be delivered for a given time, and this time can vary according to the needs from some hours to several days. In practice, in order to determine this quantity, those skilled in the art can act on two factors: the relative concentrations of biocide and organic-inorganic polymer matrix in the composite material of the invention, and the quantity of composite material. Thus, the formulation of the composite material can be modulated according to the quantity of biocide to be delivered and the duration of the treatment.

In one particular embodiment, the molar ratio between the active organic compound and the organic-inorganic polymer matrix is between 10:1 and 1:200.

In order to carry out the effluent treatment process of the invention, it can be necessary to shape the composite material of the present invention.

This shaping which is within the realm of those skilled in the art should optimize contact between the composite material of the invention and the effluent to be treated.

When using imogolite as aluminosilicate inorganic polymer, the composite material of the present invention is in gel form.

In one embodiment of the invention, the composite material in gel form is put in a container permeable to the effluent, for example a dialysis bag, a nonwoven material, etc.

This process can be used advantageously in a photographic processing method that comprises passing a silver halide photographic material through a series of processing baths between which are wash and/or stabilization baths, these baths being treated with the invention treatment process.

The process according to the present invention is particularly efficient for treating washing, stabilization, and bleaching baths or a mixture thereof.

When a photographic bath containing silver as argentodithiosulfate is treated with the process of the present invention, the silver content of the bath is reduced significantly and the formation of microorganisms is limited in a controlled way. In addition, as the pH and the salt composition of the bath are not changed, after treatment with the invention process the bath can be recycled in the photographic processing without additional treatment.

The baths thus treated can also be discharged to the sewers without additional treatment.

FIG. 1 is a schematic representation of the treatment process of the invention applied to treating a wash bath in a silver halide photographic material processing method. This figure shows a washing tank 12 containing a wash bath. The tank is fitted with a fresh bath or water inlet 21, a means of drainage 22 and a means of discharging by overflow 24. The wash bath is sent by means of the pipe 14 into a treatment cartridge 16 housing one or more containers 18 that are permeable to the wash bath and contain the composite material of the invention. At the outlet of the cartridge the solution obtained is returned by means of a pump 20 into the tank 12 where it is used again to wash photographic materials.

The wash bath recovered at the outlet of the overflow 24 or the drain 22 can be treated with a complementary treatment device 23, which can be a hydrotalcite cartridge, a nanofiltration device or an ion exchange resin. At the outlet of the device 23, a water is recovered that can be discharged to the sewers or be recycled in one of the processing baths in order to compensate for evaporation from the baths. This water can also be used to make up new baths from the concentrate. It can be necessary before using this water in a photographic bath to adjust the pH and/or the salinity of the water in order to obtain the characteristics of industrial water.

When the bath passes through the composite material, the silver is retained and the bath is charged with biocide which will limit the growth of microorganisms in the washing tank of the photographic processing.

The treatment of effluents with the composite material of the invention is carried out at a temperature between 15 and 60° C., preferably at ambient temperature.

As it is being used, the efficiency of the invention composite material reduces because the sulfur-containing sites of the invention composite material are saturated with the silver ions, and/or the quantity of biocide has been fully released into the bath. The silver contained in this composite material can then be recovered easily by firing the composite material.

In a particular embodiment, the treatment process of the invention is applied to a photographic bath containing silver in ionic form and comprises, after putting the bath into contact with the composite material of the invention, the recycling of the treated bath into the same photographic bath.

The following examples illustrate the present invention in detail.

EXAMPLE 1

Preparation of Aluminosilicate (Reference)

The aluminosilicate of this example was prepared using teachings from Patent Application WO 96/13459.

16.7 mmoles of tetraethylorthosilicate $Si(OR)_4$ were added to 1000 ml deionized water. The reaction mixture was stirred at ambient temperature for one hour, then this solution was added to 31.2 mmoles of $AlCl_3,6H_2O$ in solution in 1000 ml of pure water. The mixture was stirred for 20 minutes, then the pH was adjusted to 4.5 with 1M NaOH. The solution became cloudy. When the solution became transparent again, 1M NaOH was added until a pH equal to 6.8 was obtained. A white gel was obtained that was centrifuged for 20 minutes at 2000 rpm. The gel was collected and was put into solution with 5ml of a mixture comprising 1M HCl and 2M acetic acid. The volume was made up to 2 l with water. The solution contained 30 mmoles of Al, 16.6 mmoles of Si, 5 mmoles of HCl and 10 mmoles of acetic acid. This solution was kept at 5° C.

This solution was then diluted with deionized water to achieve a concentration in Al of 10 mmoles/l. The diluted solution was heated for 5 days at 96° C., and then it was filtered through an ultrafiltration membrane with a separation power of 10,000 Dalton (membrane manufactured by AMICON). A clear solution was obtained containing Al and Si in a ratio Al:Si of 1.8.

EXAMPLE 2

Preparation of the Composite Material of the Invention

To a solution of 3-mercaptopropyltrimethoxysilane in anhydrous methanol ($0.5 \times 10^{-3}$ mol. in 0.5 ml of methanol) containing some drops of $NH_4OH$ was added a solution of Proxel® GLX commercially available from ZENECA (0.07 g in 0.5 ml water, 14 mg of active ingredient).

According to the supplier specifications, the solution of Proxel® contains 20% by weight of an active compound of the benzisothiazolone family of the formula:

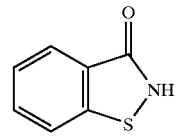

This solution was mixed with 50 ml of imogolite prepared according to the method of Example 1 and containing 2.0 g/l of (Al+Si). This solution was put into a dialysis bag, the solution geled (pH>7) and hydrolyzed in time.

The infrared spectrum of this gel shows a doubling of the Si—O bond characteristic band (1126.8 and 1035.6 $cm^{-1}$) which indicates that hydrolysis took place correctly. Moreover, the doubled band is shifted in relation to the spectrum of the polysiloxcane hydrolyzed in the absense of imogolite (bands at 1099.7 and 1042.8 $cm^{-1}$). This band shift shows that the composite material obtained is not a polysiloxane but a silane grafted onto the imogolite. In addition, the infrared spectrum of the invention material shows that the organic part is not affected by the grafting.

EXAMPLE 3

Treating Wash Baths

The composite material of Example 2 in the form of an opaque gel (50 ml) was put in a dialysis bag. The bag was put in a beaker containing 900 ml of a wash bath coming from Kodak ECP® photographic processing, after concentration with a nanofiltration system (retentate).

This concentrated wash bath contained 160 mg/l silver as argentodithiosusulfate.

The same experiment was carried out by filling the dialysis bag with the pure imogolite obtained in Example 1 (reference).

The amount of silver and the amount of Proxel® present in the bath were measured as a function of time.

The amount of silver was determined by ICP (inductively coupled plasma). The quantity of Proxel® was determined by chromatography (HPLC).

The results are given in Table 1 below. The amount of Proxel given in the table is active quantity of biocide in the solution treated.

TABLE 1

| | Invention | | Reference |
|---|---|---|---|
| Time (min) | Ag (mg/l) | Proxel ® (ml/l) | Ag (mg/l) |
| 75 | 143 | 0.32 | 141 |
| 150 | 140 | 1.15 | 140 |
| 360 | 138 | 1.17 | 146 |
| 3900 | 26.2 | 6.7 | 142 |
| 5400 | | 6.6 | |

The result obtained with the reference shows that pure imogolite only allows the quantity of silver to be reduced in very small proportions. In the case of the composite material of the present invention, the amount of silver contained in the bath is strongly reduced and the biocide is released into the treatment bath in a controlled way until a saturation value is reached. These results demonstrate the efficiency of the composite material of the invention for the treatment and maintenance of a wash bath.

What is claimed is:

1. A method for treating a photographic processing bath of a photographic processing containing silver in ionic form which comprises contacting the bath with a composite material comprising an aluminosilicate organic-inorganic polymer matrix in fiber form comprising at least on the fiber surface an organic radical having a—SH or—SH(—CH$_2$)$_n$S—function wherein n is from 0 to 4 and having dispersed therein an active organic compound.

2. The method of claim 1, which comprises, after contacting the bath with said composite material, the step of recycling the bath in the photographic processing.

3. The method of claim 2, wherein the bath is a wash or stabilization photographic bath.

4. The method of claim 1, wherein the bath is a wash, or stabilization photographic bath.

5. The method of claim 1 which further comprises the step of passing the bath through a nanofiltration system, an ion-exchange resin, or a hydrotalcite, after this bath has been contacted with said composite material.

* * * * *